United States Patent
Fernkvist et al.

(10) Patent No.: US 9,402,772 B2
(45) Date of Patent: Aug. 2, 2016

(54) ABSORBENT ARTICLE CONTAINING A BREATHABLE MATERIAL LAYER

(75) Inventors: Maria Fernkvist, Mölndal (SE); Ingrid Gustafson, Åsa (SE); Charlotta Hansson, Göteborg (SE)

(73) Assignee: SCA HYGIENE PRODUCTS AB, Gothenburg (SE)

( * ) Notice: Subject to any disclaimer, the term of this patent is extended or adjusted under 35 U.S.C. 154(b) by 1829 days.

(21) Appl. No.: 12/513,771

(22) PCT Filed: Dec. 7, 2007

(86) PCT No.: PCT/SE2007/050957
§ 371 (c)(1),
(2), (4) Date: May 6, 2009

(87) PCT Pub. No.: WO2008/069752
PCT Pub. Date: Jun. 12, 2008

(65) Prior Publication Data
US 2010/0042062 A1      Feb. 18, 2010

(30) Foreign Application Priority Data

Dec. 8, 2006    (WO) ................. PCT/SE2006/001405

(51) Int. Cl.
*A61F 13/15*      (2006.01)
*A61F 13/514*     (2006.01)

(52) U.S. Cl.
CPC ..... *A61F 13/51403* (2013.01); *A61F 13/51401* (2013.01); *A61F 13/51458* (2013.01)

(58) Field of Classification Search
USPC .................................................. 604/361, 367
See application file for complete search history.

(56) References Cited

U.S. PATENT DOCUMENTS

| | | | |
|---|---|---|---|
| 3,881,489 A | 5/1975 | Hartwell |
| 3,929,135 A | 12/1975 | Thompson |
| 4,341,216 A | 7/1982 | Obenour |
| 4,591,523 A | 5/1986 | Thompson |
| 4,637,819 A | 1/1987 | Ouellette et al. |
| 4,982,450 A | 1/1991 | D'Huissier |

(Continued)

FOREIGN PATENT DOCUMENTS

| | | |
|---|---|---|
| EP | 0293482 A1 | 12/1988 |
| EP | 0710471 A1 | 5/1996 |

(Continued)

OTHER PUBLICATIONS

International Search Report (PCT/ISA/210) for PCT/SE2007/050957, completed Apr. 2, 2004.

(Continued)

*Primary Examiner* — Susan Su
(74) *Attorney, Agent, or Firm* — Buchanan Ingersoll & Rooney PC

(57) ABSTRACT

An absorbent article includes a breathable backsheet material layer. At least a part of the layer includes a polymeric material exhibiting a discontinuous change in free volume in response to any of the following conditions or variables: liquid contact, the presence of certain ions, temperature and/or pH. One example of such polymeric materials is side chain liquid crystalline polymers which are able to undergo a phase transition between an isotropic phase and a nematic phase. The discontinuous change in free volume involves an abrupt change of the permeability of the breathable material layer.

12 Claims, 1 Drawing Sheet

(56) References Cited

U.S. PATENT DOCUMENTS

| | | | |
|---|---|---|---|
| 5,447,788 | A | 9/1995 | Rhim et al. |
| 5,770,528 | A | 6/1998 | Mumick et al. |
| 5,955,187 | A | 9/1999 | McCormack et al. |
| 5,969,052 | A * | 10/1999 | Mumick ............... A61L 15/24 525/329.9 |
| 6,420,625 | B1 | 7/2002 | Jones et al. |
| 6,436,508 | B1 | 8/2002 | Ciammaichella et al. |
| 6,565,549 | B1 * | 5/2003 | Allen et al. ............ 604/385.04 |
| 2002/0155771 | A1 * | 10/2002 | Soane et al. .................. 442/79 |
| 2003/0161995 | A1 | 8/2003 | Kauschke et al. |
| 2006/0154544 | A1 | 7/2006 | Talingting-Pabalan et al. |

FOREIGN PATENT DOCUMENTS

| | | |
|---|---|---|
| EP | 0710472 A1 | 5/1996 |
| EP | 0846454 A1 | 6/1998 |
| EP | 1040800 A1 | 10/2000 |
| EP | 1238714 B1 | 3/2005 |
| GB | 2333724 A | 8/1999 |
| JP | 11-348163 | 12/1999 |
| JP | 2000-512872 A | 10/2000 |
| JP | 2001-507736 A | 6/2001 |
| JP | 2001-510710 | 8/2001 |
| JP | 2002-508215 | 3/2002 |
| JP | 2004-154333 A | 6/2004 |
| JP | 2005-507306 A | 3/2005 |
| WO | 94/24196 A1 | 10/1994 |
| WO | WO 97/24150 A1 | 7/1997 |
| WO | 97/48360 A1 | 12/1997 |
| WO | 98/29461 A1 | 7/1998 |
| WO | WO 99/03435 A1 | 1/1999 |
| WO | WO 99/04739 A1 | 2/1999 |
| WO | WO 99/12734 A1 | 3/1999 |
| WO | WO 99/30657 | 6/1999 |
| WO | WO 00/39201 A2 | 7/2000 |
| WO | WO 00/59434 A1 | 10/2000 |
| WO | 02/098571 A2 | 12/2002 |
| WO | WO 2005/021262 | 3/2005 |

OTHER PUBLICATIONS

Written Opinion (PCT/ISA/237) for PCT/SE2007/050957, completed Apr. 2, 2004.

Hoffman, "Intelligent" Polymers, Controlled Drug Delivery, Chapter 24, 1997, American Chemical Society, pp. 485-498.

Schneider et al., "Dimension Changes in a Chemomechanical Polymer Containing Ethylenediamine and Alkyl Functions as Selective Recognition Units" Eur. J. Org. Chem., 2006, pp. 677-692.

D2 Article 1: V. Saez et al., "Liberacion Controlada de Farmacos Hidrogeles," vol. 4(1), Revista Iberoamericana de Polimeros (2003) pp. 21-76.

Office Action issued in corresponding Colombian Application No. 09070161 on Aug. 9, 2012.

Patent Examination Report No. 1, issued in corresponding Australian application No. 2007328527, dated Mar. 6, 2013, 3 pages.

Office Action issued in corresponding Japanese Application No. 2009-540209, mailed Jun. 20, 2012.

Office Action (Decision of Rejection) issued on Jun. 9, 2014, by the Japanese Patent Office in corresponding Japanese Patent Application No. 2013-037075, and an English Translation of the Office Action. (3 pages).

Tirrell, David A. "Macromolecular Switches for Bilayer Membranes", Journal of Controlled Release, 6 (1987) pp. 15-21, Elsevier Science Publishers B.V., Amsterdam.

Iwata, Hiroo et al., "Preparation of Temperature-Sensitive Membranes by Graft Polymerization onto a Porous Membrane" Journal of Membrane Science, 55 (1991) pp. 119-130, Elsevier Science Publishers B.V., Amsterdam.

Osada, Yoshihito et al., Control of Water Permeability by Mechanochemical Contraction of Poly(methacrylic acid)-Grafted Membranes, Journal of Membrane Science, 27 (1986) pp. 327-338, Elsevier Science Publishers B.V., Amsterdam.

Yoshida, Masaru et al., "Stimulus-Responsive Track Pores", Radiation Effects and Defects in Solids, 1993, vol. 126, pp. 409-412, 1993 copyright Gordon and Breach S.A. Printed in the USA.

Japanese Office Action (Notice of Reasons for Rejection) dated Feb. 17, 2014, issued in corresponding Japanese Application No. 2013-037075. (5 pgs).

* cited by examiner

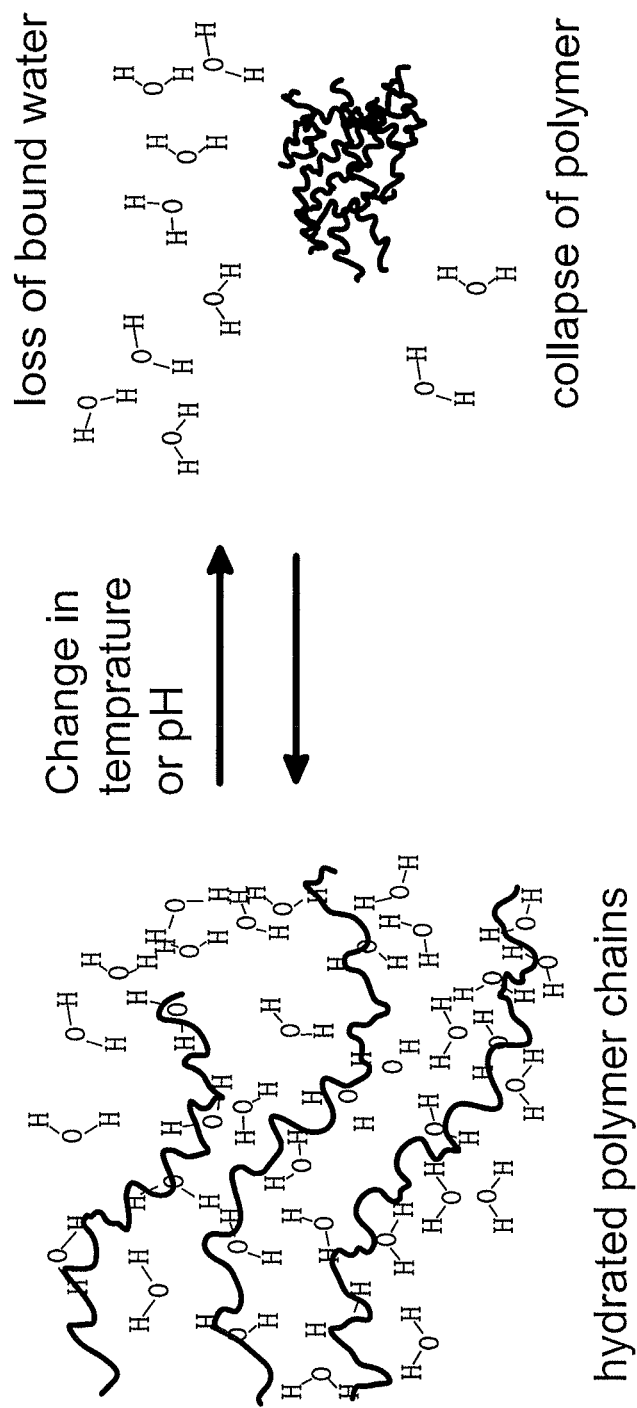

ABSORBENT ARTICLE CONTAINING A BREATHABLE MATERIAL LAYER

TECHNICAL FIELD

The present invention refers to an absorbent article for absorption of bodily exudates, such as a diaper, sanitary napkin, incontinence guard, absorbent pants, pantiliner etc., said article having an absorbent structure and a breathable backsheet material underlying said absorbent structure.

BACKGROUND OF THE INVENTION

Breathable materials are materials, that provide moisture vapour permeability and preferably are barriers to liquid. Such materials are often used as backsheet materials in absorbent articles like diapers, sanitary napkins, incontinence guards, absorbent pants, pantiliners etc. Examples of breathable liquid barrier materials are microporous films, apertured formed films and fibrous nonwoven materials comprising a barrier layer of fine fibers, usually so called meltblown fibers. Such nonwoven materials may be in the form of a so called SMS (spunbond-meltblown-spunbond) laminate comprising an inner meltblown barrier layer and outer spunbond layers. Breathable liquid barrier materials may also be in the form of laminates between films and fibrous nonwovens. The incorporation of breathable backsheet materials allows for the transfer of moist air from the article, which increases comfort and reduces the risk for skin irritations.

The main drawback associated with breathable backsheet materials in absorbent articles is the negative effect on the protection level against leakage in the form of liquid wetting through the breathable backsheet and soiling the wearer's undergarment. Even if these materials are intended to only allow the passage of gases therethrough, some liquid may also pass through due to physical mechanisms like diffusion and capillary action. Such leakage of liquid through a breathable backsheet material may become more frequent when the article is heavily loaded with discharged body liquid and when used during physical exercise. Even if liquid does not actually penetrate through the backsheet material a high breathability may result in condensation on the outside of the backsheet material, which gives a wet feeling.

This problem has been recognized in the prior art and different solutions have been suggested for reducing the problem of leakage of liquid through a breathable backsheet material. Thus it has been proposed in U.S. Pat. No. 4,341,216, EP 710 471 and EP 710 472 to use breathable backsheets comprising at least two breathable material layers.

WO 99/04739 suggests another solution, namely that the breathable backsheet material has at least one region thereof coated with a non soluble, liquid swellable material. Upon contact with liquid discharge the material will swell and close the apertures therethrough, thereby reducing air permeability and preventing the passage of liquid through the layer.

U.S. Pat. No. 5,447,788 discloses a fibrous nonwoven web in which a certain proportion of the fibers are prepared from a liquid-swellable polymer. In the presence of liquid these fibers will swell to substantially block the passage of liquid through the web. The web may be used as a breathable backsheet material.

U.S. Pat. No. 5,955,187 discloses a microporous film which includes a plurality of fine water-swellable filler particles in its pores, that will swell upon liquid contact.

U.S. Pat. No. 6,436,508 discloses a breathable backsheet material in the form of an apertured film or a fibrous layer coated with a liquid swellable material, for example polyvinyl alcohol.

Liquid swelling is however a rather slow process based on diffusion, which means that leakage may occur through the material layer before swelling has taken place.

OBJECT AND MOST IMPORTANT FEATURES OF THE INVENTION

The present invention aims at providing an alternative solution to the problem of reducing the risk for leakage of liquid through a breathable backsheet material layer. This has according to the invention been provided by the fact that at least part of said breathable backsheet material comprises a polymeric material exhibiting a discontinuous change in free volume in response to any of the following conditions or variables: liquid contact, the presence of certain ions, temperature and/or pH.

An advantage of the present invention is that this discontinuous change in free volume is a rapid process, considerably faster than liquid swelling, which is a continuous process. In addition the layer may maintain at least a degree of moisture vapour permeability also after the discontinuous change in free volume.

The material layer is selected from apertured films, microporous films, macroporous films, nanoporous films, monolithic films, fibrous nonwovens and laminates therefrom.

According to one embodiment the polymeric material exhibiting a discontinuous change in free volume is applied in the form of a coating to at least one surface or region of said material layer.

In one aspect of the invention the areas adjacent and/or within the apertures/pores of the material layer are coated with the polymeric material exhibiting a discontinuous change in free volume.

According to one embodiment the non-swelling topology changing polymeric material is a side chain liquid crystalline polymer which is able to undergo a phase transition between an isotropic phase and a nematic phase at selected temperatures.

According to a further embodiment at least part of the backsheet material is a nanoporous or monolithic film comprising a side chain liquid crystalline polymer material.

According to a still further embodiment said breathable backsheet material has a lower degree of breathability after a discontinuous change in free volume caused by wetting with body fluid. This reduction should be at least a 10% reduction of the Water Vapour Transmission Rate (WVTR) in $g/m^2$, 24 hours, according to ASTM D 6701-01 at 23° C. Preferably the reduction is at least 30% and more preferably at least 70%.

In one aspect of the invention the discontinuous change in free volume is triggered by a change in temperature caused by contact with body liquid, such as urine or menstrual fluid.

DESCRIPTION OF DRAWING

FIG. 1 illustrates schematically the change in free volume in a polymeric material upon change of temperature or pH

DEFINITIONS

Breathable

The term "breathable" refers to air permeable and water vapour permeable materials. Preferably the materials are resistant to penetration of liquids or have liquid barrier properties.

Swelling

The term "swelling" refers to the increase of volume of a material caused by the absorption of a liquid. Swelling is a continuous process which usually occurs isotropically in xyz-direction.

Free Volume

The term free volume of a material refers to the difference $v-v_o$ ie between the total volume of a material and the actual volume $v_o$ occupied by atoms and molecules.

The free volume of a polymeric material could be measured by using positron annihilation lifetime spectroscopy (PALS). Using PALS with thin films, an electrostatically focused beam of several keV positrons generated in a high vacuum system, is implanted in the material. The positrons slow down through collisions in the material from its initial beam energy (several keV) to several eV. The reduced energy due to collisions, can be correlated with void size and form the basis of this technique.

Discontinuous Change in Free Volume

The change in free volume referred to is an abrupt change triggered by any of the following conditions or variables: liquid contact, the presence of certain ions, temperature and/or pH. This change in free volume does not depend on swelling caused by the absorption of liquid. At least in some cases the change in free volume occurs substantially anisotropically in xy-direction.

DESCRIPTION OF PREFERRED EMBODIMENTS

The breathable materials according to the present invention may be an apertured film, a microporous film, a macroporous film, a nanoporous film, a monolithic film, a fibrous nonwoven and laminates therefrom. The apertures or pores may be of varying dimensions, but typically the apertures for microporous and macroporous films are of an average diameter of from 5 µm to 600 µm. For example 2-dimensional planar microporous films for use as a breathable layer according to the invention may have apertures having diameters from 5 µm to 200 µm and suitable 2-dimensional macroporous films have an average diameter of from 90 µm to 600 µm. The apertures are preferably evenly distributed across the entire surface of the layer, but may also be distributed only in certain regions of the layer. Suitable microporous and macroporous films may be produced by any known method in the art, for example as disclosed in EP 293 482.

Apertured formed films include films having discrete openings which extend beyond the horizontal plane of the layer thus forming protuberances, which may be of a funnel-shape, such as disclosed in U.S. Pat. No. 3,929,135. Other examples of suitable macroscopically expanded films are described in U.S. Pat. No. 4,637,819 and U.S. Pat. No. 4,591,523.

Nanoporous films are films having pores with an average diameter smaller than 1 µm. Nanoporous films may be produced by micromechanical deformation, with similar techniques as for microporous and macroporous films, for example by stretching of filled polymer, wherein said filler is in the form of inorganic particles embedded in the polymer. Instead of inorganic particles an immiscible polymer may be introduced in the polymer matrix.

Monolithic films offer a generally uniform construction which is free from pores. Monolithic breathable films are capable of allowing the transfer of certain gases and liquid vapours through the film due to free volume between the polymer chains. A high rate of moisture transmission is driven by the relatively high concentration and pressure of vapour on one side of the film.

Conventional monolithic films require a change in the thickness of the film in order to modify the water vapour transmission rate (WVTR) performance, with thinner films providing higher WVTR values.

Examples of nonwoven materials having liquid barrier properties are webs made from meltblown fibers having a fineness generally smaller than 10 microns in average diameter, and laminates of meltblown webs and other webs, for example spunbond webs.

Suitable breathable materials may also be in the form of laminates between apertured, microporous, macroporous, nanoporous or monolithic films and nonwoven webs.

The breathable material should have a water vapour transmission when dry of at least 500 $g/m^2$, 24 hours when measured according to ASTM D 6701-01 at 23° C.

According to the present invention the breathable material comprises a polymeric material exhibiting an abrupt discontinuous change in free volume in response to any of the following conditions: liquid contact and/or the presence of certain ions and/or when passing certain threshold values for temperature and/or pH. This discontinuous change in free volume is different from a swelling process, wherein liquid is absorbed into a structure causing a continuous change of volume of the material.

The term liquid as used herein refers to any fluid containing at least 75% by weight of water, such as body fluids including urine, menstrual fluid, faeces and the like.

It would according to one embodiment of the invention be possible that the polymeric material exhibits both a discontinuous change in free volume and swelling properties caused by absorption of liquid.

The entire or only part of the breathable material may be composed of said polymeric material exhibiting a discontinuous change in free volume.

The polymeric material exhibiting a discontinuous change in free volume may further be applied as a coating to at least certain regions of the breathable material. It may for example be applied to only one side surface of the material or only in the areas around and/or within the apertures of the breathable material.

When the breathable material is a fibrous nonwoven web all or a certain proportion of the fibres may be of the polymeric material exhibiting a discontinuous change in free volume. Said polymeric material may alternatively be applied as a coating on individual fibers or on the entire or certain regions of the nonwoven web.

The free volume in a polymeric material is defined as the volume in the polymeric material that is not occupied by polymer molecules and is measured by positron annihilation lifetime spectroscopy (PALS) as described above. The discontinuous change in free volume is a very rapid and abrupt process and occurs much more rapidly than for example swelling caused by absorption of liquid, which is a continuous process taking place during a period of time of several seconds or minutes. Examples of suitable polymers can be found in the following groups of polymers:

Side Chain Liquid Crystalline Polymers

Side chain liquid crystalline polymers suitable for the purpose of the present invention are polymers which are able to undergo a temperature-induced phase transition changing the permeability properties of the polymer. The phase transition occurs between an isotropic phase and a nematic phase at selected temperatures. In its nematic phase the side chains tend to be parallel to a common axis, while in its isotropic phase the side chains are randomly orientated in all directions, which means a more space requiring configuration. This means that the free volume that is not occupied by the polymer molecules is larger in the isotropic than in the nematic phase, and thus the permeability properties of the polymer will change when the material changes phase.

Examples of side chain liquid crystalline polymers are derived from (i) at least one n-alkyl acrylate or methacrylate in which the n-alkyl group contains at least 12 carbons and (ii) one or more comonomers selected from acrylic acid, methacrylic acid and esters of methacrylic or acrylic acids. Specific examples are copolymers obtained by radical copolymerization in butylacetate of 50 mole % of an acrylate monomer bearing a long (C2H4-C8F17) perfluoro side chain and 50 mole % of a methacrylate monomer bearing a long alkyl chain, for example C17 H35. Such polymers are able to undergo a phase transition from a nematic phase to an isotropic phase at a temperature of around 35° C., thus close to body temperature. This phase transition takes place rapidly when the temperature threshold is passed. The phase transition is usually reversible.

Other examples of temperature responsive side chain liquid crystalline polymers which can be used are available from Landec Corp. under the trade name Intelimer®.

The temperature switch can for example be triggered by a change in temperature caused by contact with body liquid. This change may either be caused by the temperature of the liquid itself or caused by an evaporation effect. When the liquid evaporates a cooling effect is obtained, so that the temperature in the area where the polymer is in contact with the evaporating liquid will be lowered. When reaching its phase transition temperature the polymer will undergo an abrupt discontinuous change in free volume and switch to a nematic (crystalline) phase, in which the free volume between the polymer chains is smaller. The phase transition is in such a case obtained by a temperature change caused by liquid contact.

Polymers or Gels Possessing Low Critical Solution Temperature (LCST) in Water Solutions The definition of Low Critical Solution Temperature (LCST) is the critical temperature for the polymer, below which a linear polymer is miscible with the solvent and above which the polymer is immiscible i.e. the polymer precipitates.

The temperature of e.g. poly(N-isopropylacrylamide), polyNIPA, has an effect on its chemistry. PolyNIPA has two functional groups, an isopropylic group and an amide group. Below the LCST, the hydrogen bonding between the amide group and the water allow the polyNIPA to be soluble in water and hydrophilic. Above the LCST, there are hydrophobic interactions in the isopropyl group which causes the polymer to become hydrophobic and to collapse into itself. To keep the polymer in this formation, the critical temperature must be maintained. Reverting back to lower temperature would result in the mixing of the polymer and solvent into solution until critical temperature is reached again.

This phenomenon for chemically crosslinked gels is manifested as being below LCST, wherein the gel is fully hydrated and swollen. Above LCST the gel precipitates and shrinks. This is illustrated in FIG. 1. The passage of LCST is discontinuous and has a tremendous impact on the free volume of the gel.

Chemically crosslinked polyNIPA is an example. PolyNIPA gel having a LCST of about 34° C. can be synthesized in the following way:

Prepare a 10-25 wt % n-NIPA solution in distilled water using an Erlenmayer flask (250 ml). Add a crosslinker in the form of 1-5 mole % MBA to the dissolved NIPA solution. Transfer the solution into a 50 ml glass vial and bubble nitrogen gas during 1 min. through the solution. Add an initiator, $K_2S_2O_8$, to the solution and bubble nitrogen gas during 1 min. Close the glass vial and shake it at 30° C. for 12 hours. Put the gel into distilled water during night and extract it in acetone. Dry the polymer in room temperature or in a vacuum at 30° C.

Temperature and pH Sensitive Polymers

Certain copolymers containing both temperature and pH sensitive groups can be tailored so that the LCST phenomenon of the temperature-sensitive component is more or less eliminated when the pH is raised above the pK of the pH-sensitive component. It has been shown (Allan S. Hoffman; *Controlled Drug Delivery, Chapter 24: "Intelligent" polymers,* 1997, American Chemical Society) that only a small amount, e.g. 10 mol %, of a pH-sensitive monomer may be sufficient to eliminate the LCST phenomenon of the major, temperature-sensitive component when the pH is raised above the pK of the pH-sensitive component. Examples of such polymers are random copolymers of N-isopropyl acrylamide (NIPAAm) and acrylic acid (AAc), wherein NIPAAm is the temperature-sensitive component and AAc the pH-sensitive component. Preferred examples are random copolymers of 80-98 weight % and preferably 85-95 weight % NIPAAM and 2-20 weight % and preferably 5-15 weight % AAc. Such copolymers have a LSCT slightly below body temperature at a pH of 4.0 and a LCST at a considerably higher temperature, above 60° C., at pH of 7.4. The LCST of the polymer may be set by adjusting the amount of the pH-sensitive component in the polymer. Such a polymer may be suitable to use in acid conditions, for example in absorbent articles containing acid components such as an acid superabsorbent material.

Ion Sensitive Polymers

Polymers are known which undergo a dimensional change in contact with certain ions. One example is polymethyl methacrylate treated with dodecylamine and dodecyltriamine producing a chemomechanical polymer, which undergoes large macroscopic motions upon contact with certain ions in an aqueous solution. The ions may be $Na^+$ and $Cl^-$ ions which are present in urine. Such polymers are described in: H-J. Schneider, L. Tianjun and N. Lomadze: *Eur. J. Org. Chem.* 2006, p. 677-692: *"Dimension Changes in a Chemomechanical Polymer Containing Ethylenediamine and Alkyl Functions as Selective Recognition Units"*. This polymer is also pH-sensitive.

Further examples of ion- and/or pH-sensitive polymers are certain proteins like collagen.

Examples of Breathable Materials

The breathable material according to the invention may be accomplished in many different ways, as explained above, e.g. apertured films, microporous films, macroporous films, nanoporous films, monolithic films, fibrous nonwovens and laminates therefrom. One example of a breathable material useful as backsheet material in an absorbent article is a nanoporous or a monolithic film of Intelimer® polymer available from Landec Corp. The film may entirely be of said polymer or it may be combined with other polymers.

The Intelimer® polymer will undergo a discontinuous change of free volume at a temperature which is selected to be slightly above the wet temperature for body liquid, such as urine or blood, i.e. in the temperature range 5-50° C. depending on the environmental temperature. Above this temperature the polymer will have an isotropic (amorphous) structure in which the free volume between the polymer chains is large enough to let air and water vapour pass therethrough. When the absorbent article is wetted by body liquid and the liquid reaches the backsheet material, an evaporation process will start as the body liquid starts to evaporate and the vapours escape through the backsheet. This will result in a cooling effect, so that the temperature in the area where the backsheet is in contact with the evaporating body liquid will be lowered to the wet temperature for body fluids like urine and blood. When reaching this temperature the polymer will undergo an abrupt discontinuous change in free volume and switch to a nematic (crystalline) phase, in which the free volume between the polymer chains is smaller and thus the permeability of the film is decreased. This will lead to a rapid and effective sealing effect reducing the risk for leakage of liquid through the backsheet. The permeability to air and vapours will of course also be reduced, but may be maintained to a certain degree.

Another example of a breathable material useful as a backsheet material in an absorbent article is an apertured or porous film, especially a microporous or macroporous film, in which only the apertures or pores are coated with a side chain liquid crystalline polymer, e.g. an Intelimer® polymer, which is able to undergo a discontinuous change of free volume at a temperature slightly below body temperature, i.e. in the temperature range 20-40° C., preferably 25-35° C. When said polymer is in its nematic (crystalline) state it will take up a smaller region of the opening area of the apertures or pores which means that the permeability to air and water vapour and thus the breathability is high. However when discharged body liquid of a temperature close to body temperature comes in contact with the film and the side chain liquid crystalline polymer, said polymer will immediately switch to its isotropic (amorphous) structure in which the free volume between the polymer chains is larger and the polymer therefore will fill up a relatively larger part of the opening area of the apertures or pores. This will lead to an effective sealing against leakage of liquid through the film. The permeability to air and vapours will of course also be reduced, but may be maintained at least to some degree.

In a still further example of a breathable backsheet material according to the invention polyNIPA is applied for example as a thin film onto a nonwoven material. It is applied and solidified from its more space requiring state thereby giving a nonwoven material that is readily breathable. When wetted with body fluids the polyNIPA film will pass into its LCST and switch to its more contracted state, thus bringing the fibres in the nonwoven material closer together and reducing the average pore size in the nonwoven material. PolyNIPA may be used either in the form of linear polyNIPA or in gel form. Instead of polyNIPA a pH- and/or ion sensitive polymer like collagen may be used.

Breathable Backsheet Materials in Absorbent Articles

The breathable material according to the invention is used as a breathable backsheet in absorbent articles like diapers, sanitary napkins, incontinence guards, absorbent pants, pantiliners etc. Such article typically comprises a liquid permeable topsheet material, a liquid impermeable backsheet material and an absorbent core enclosed there between. The use of breathable materials as backsheet in absorbent articles allows for the passage of gases, e.g. water vapour or air, there through. Thus before use and whilst the backsheet remains dry, the absorbent article is permeable to water vapour and air. After contact with body liquid, the polymeric material exhibiting a discontinuous change in free volume will rapidly switch between a less and a more bulky and space requiring structure having a larger free volume and vice versa in any of the manners described above and thus tending to reduce the size of the apertures in the material and thus the permeability of the breathable material. The permeability to air, water vapour and/or liquid will be reduced. Since the change in free volume will only take place in those areas of the material which have been in contact with body fluid, the moisture vapour permeability will be maintained in other areas of the material, so that the material will maintain at least a degree of moisture vapour permeability also after the change of free volume.

Due to the incorporation of polymeric materials exhibiting a discontinuous change in free volume in breathable backsheets, the permeability and thus the breathability of the material can be allowed to be higher than in conventional breathable backsheet materials without leakage or condensation, since as soon as the material is exerted to discharged body fluid the apertures in only those parts of material that is wetted by the fluid will be reduced in size and prevent leakage of liquid therethrough, either caused by the liquid contact as such or due to the temperature change caused by the contact with body fluid or a combination of both. Thus higher porosity may be allowed in a material according to the invention than in conventional breathable backsheet materials, and still avoiding leakage of liquid. This means a higher comfort to the wearer due to the improved breathability and a higher security against leakage of body fluid through the breathable backsheet.

The discontinuous change in free volume may also be caused by the presence of ions in the body fluid and/or a change of pH.

The polymeric material exhibiting a discontinuous change in free volume may be applied only in selected regions of the breathable backsheet. It may for example be applied only on one side surface of the backsheet, preferably on the side surface intended to be located towards the absorbent core of the article. This ensures that the polymeric material contacts the body fluid as soon as it has passed through the absorbent core and can immediately switch its free volume, thus preventing wet through of the body fluid. It may further only be applied in the areas around and/or within the apertures of the breathable backsheet. Additional backsheet layers may be positioned on the wearer facing or the garment facing side of the breathable backsheet material, said additional layers should of course also be breathable, but need not necessarily contain any polymeric material exhibiting a discontinuous change in free volume.

Laboratory Test

A laboratory test on porous materials treated with the temperature responsive polymer EHEC was made to examine the effect of temperature (below and above the LSCT of EHEC) on the liquid permeability of the porous materials.

Test Solution:

Dissolve 2 wt % EHEC (ethyl hydroxyethyl cellulose) DVT 96002 (LCST~34.5° C.) in water.

Test Samples:

Filter paper Lot no 4042169 from Hollingsworth & Vose and nonwoven-T2 (NW-T2) 50 gsm from Libeltex.

Treating:

The samples were immersed in the test solution for 10 min. They were subsequently dried in room temperature.

Instrument Used:

Thermometer, Microtherma 2, Hotplate-Labotech EM3300T, Timer, Finnpipette-0.5 μl-10 μl and 20 μl 1-200 μl.

Test Set-Up:

Two different surface temperatures were tested. In one case the surface temperature was below the LCST of EHEC and in the other one it was above. The cold surface had a temperature of 23° C. and the warm surface had a temperature of about 38° C. A droplet of 0.9% NaCl solution at two different temperatures, 37° C. or 23° C., was placed on the treated surface and the time for the droplet to be absorbed/evaporated was measured. Different sizes of the droplets were tested, between 5 μl-50 μl. Results are shown in table 1.

Absorption of a cold droplet on a cold surface took place after 150 sec. For warm droplets placed on a warm surface, a temperature above LCST for the polymer, no absorption took place. A droplet at a size of 5 μl was evaporated after 1450-1500 sec. The delay or disappearance of absorption when working above the LCST of EHEC is related to a decrease in free volume of the polymer, since when the free volume decreases the warm droplet is not absorbed. When working below LCST (the cold droplet and surface) absorption took place after 150 sec. When working above LCST (the warm droplet and surface) the droplet is not absorbed but evaporated after 1450 sec.

TABLE 1

| Treated filter paper, surface temperature 38° C. droplet temperature 37° C. | |
|---|---|
| A droplet of 5 μl, 37° C. 0.9% NaCl is placed on the treated filter paper with a surface temperature of 38° C. | Evaporated after 1800 sec. |
| A droplet of 50 μl, 37° C. 0.9% NaCl is placed on the treated filter paper with a surface temperature of 38° C. | Droplet stays on the surface until it evaporates- no time measured. |
| Treated filter paper, surface temperature 23° C. Droplet temperature 23° C. | |
| A droplet of 50 μl, 23° C. 0.9% NaCl is placed on the treated filter paper with a surface temperature of 23° C. | Absorbed after 160 sec. |
| Treated NW, surface temperature 38° C. droplet temperature 37° C. | |
| A droplet of 5 μl, 37° C. 0.9% NaCl is placed on the treated NW-T2 with a surface temperature of 38° C. | Evaporated after 1500 sec. Evaporated after 1550 sec. |
| A droplet of 10 μl, 37° C. 0.9% NaCl is placed on the treated NW-T2 with a surface temperature of 38° C. | Evaporated after 1440 sec. |
| A droplet of 20 μl, 37° C. 0.9% NaCl is placed on the treated NW-T2 with a surface temperature of 38° C. | Evaporated after 1500 sec. |
| A droplet of 50 μl, 37° C. 0.9% NaCl is placed on the treated NW-T2 with a surface temperature of 38° C. | Droplet stays on the surface until it evaporates - no time measured |
| Treated NW, surface temperature 23° C. droplet temperature 23° C. | |
| A droplet of 5 μl, 23° C. 0.9% NaCl is placed on the treated NW-T2 with a surface temperature of 23° C. | Absorbed after 140 sec. |

The invention claimed is:

1. An absorbent article for absorption of bodily exudates, said article comprising an absorbent structure and a breathable backsheet material underlying said absorbent structure, wherein at least a part of said breathable backsheet material comprises a polymeric material exhibiting a discontinuous change in free volume in response to any of the following conditions or variables: liquid contact, the presence of certain ions, or change of pH.

2. An absorbent article according to claim 1, wherein said backsheet material is selected from the group consisting of apertured films, microporous films, macroporous films, nanoporous films, monolithic films, fibrous nonwovens and laminates therefrom.

3. An absorbent article according to claim 1, wherein said polymeric material exhibiting a discontinuous change in free volume is applied in the form of a coating to at least one surface or region of said backsheet material.

4. An absorbent article according to claim 3, wherein regions adjacent and/or within apertures/pores of the backsheet material are coated with said polymeric material exhibiting a discontinuous change in free volume.

5. An absorbent article according to claim 1, wherein said breathable backsheet material has a lower degree of breathability after a discontinuous change in free volume caused by wetting with body fluid.

6. An absorbent article according to claim 5, wherein the body fluid comprises urine or menstrual fluid.

7. An absorbent article according to claim 1, wherein the absorbent article is a diaper, sanitary napkin, incontinence guard, absorbent pants, or pantiliner.

8. An absorbent article according to claim 1, wherein the conditions or variables is liquid contact.

9. An absorbent article according to claim 1, wherein the conditions or variables is the presence of certain ions.

10. An absorbent article according to claim 1, wherein the conditions or variables is change of pH.

11. An absorbent article for absorption of bodily exudates, said article comprising an absorbent structure and a breathable backsheet material underlying said absorbent structure, wherein at least a part of said breathable backsheet material comprises a polymeric material exhibiting a discontinuous change in free volume in response to any of the following conditions or variables: liquid contact, the presence of certain ions, change of temperature or change of pH,
    wherein said polymeric material exhibiting a discontinuous change in free volume is a side chain liquid crystalline polymer which is able to undergo a phase transition between an isotropic phase and a nematic phase at selected temperatures.

12. An absorbent article according to claim 11, wherein at least a part of the backsheet material is a nanoporous or monolithic film comprising a side chain liquid crystalline polymer material.

* * * * *